United States Patent
Sathaye (10) Patent No.: US 7,778,696 B2
(45) Date of Patent: Aug. 17, 2010

(54) SELECTION OF CARDIAC CAPTURE VERIFICATION MODES

(75) Inventor: Alok Sathaye, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 763 days.

(21) Appl. No.: 11/284,216

(22) Filed: Nov. 21, 2005

(65) Prior Publication Data

US 2007/0118181 A1 May 24, 2007

(51) Int. Cl.
*A61B 5/04* (2006.01)
(52) U.S. Cl. .................................................. 600/509
(58) Field of Classification Search ................. 600/509
See application file for complete search history.

(56) References Cited

U.S. PATENT DOCUMENTS

| | | | | |
|---|---|---|---|---|
| 4,969,467 A * | 11/1990 | Callaghan et al. | ............. | 607/28 |
| 5,954,756 A * | 9/1999 | Hemming et al. | ............. | 607/28 |
| 6,324,427 B1 | 11/2001 | Florio | | |
| 6,512,953 B2 * | 1/2003 | Florio et al. | .................. | 607/28 |
| 6,865,421 B2 * | 3/2005 | Bradley | ........................ | 607/27 |
| 6,947,794 B1 * | 9/2005 | Levine | ......................... | 607/28 |
| 7,162,301 B2 * | 1/2007 | Kim et al. | ..................... | 607/28 |
| 7,203,543 B2 * | 4/2007 | Meyer et al. | .................. | 607/28 |
| 7,212,855 B1 * | 5/2007 | Kroll et al. | ...................... | 607/4 |
| 7,280,868 B2 * | 10/2007 | Rueter et al. | .................. | 607/9 |
| 7,286,876 B2 * | 10/2007 | Yonce et al. | .................. | 607/28 |
| 7,319,900 B2 * | 1/2008 | Kim et al. | ..................... | 607/27 |
| 7,337,000 B2 * | 2/2008 | Meyer et al. | .................. | 607/27 |
| 7,363,081 B1 * | 4/2008 | Kroll et al. | .................... | 607/28 |
| 7,392,088 B2 * | 6/2008 | Dong et al. | .................... | 607/28 |
| 7,412,287 B2 * | 8/2008 | Yonce et al. | .................. | 607/28 |
| 7,574,258 B2 * | 8/2009 | Sih et al. | ......................... | 607/5 |
| 2002/0087200 A1 * | 7/2002 | Zhu et al. | ..................... | 607/27 |
| 2004/0088018 A1 | 5/2004 | Sawchuk et al. | | |
| 2004/0172065 A1 * | 9/2004 | Sih et al. | ......................... | 607/4 |
| 2005/0131478 A1 * | 6/2005 | Kim et al. | ..................... | 607/27 |
| 2006/0122681 A1 * | 6/2006 | Kroll et al. | .................. | 607/123 |
| 2006/0129195 A1 * | 6/2006 | Sathaye et al. | ................ | 607/17 |
| 2006/0155338 A1 * | 7/2006 | Mongeon et al. | ............... | 607/9 |
| 2006/0247693 A1 * | 11/2006 | Dong et al. | .................... | 607/9 |
| 2006/0247695 A1 * | 11/2006 | Stalsberg et al. | ............... | 607/9 |
| 2006/0247696 A1 * | 11/2006 | Stalsberg et al. | ............... | 607/9 |
| 2006/0247707 A1 * | 11/2006 | Meyer et al. | .................. | 607/28 |
| 2006/0287685 A1 * | 12/2006 | Meyer et al. | .................. | 607/28 |
| 2006/0293717 A1 * | 12/2006 | Sathaye et al. | ................ | 607/28 |
| 2007/0016261 A1 * | 1/2007 | Dong et al. | .................... | 607/28 |
| 2007/0078489 A1 * | 4/2007 | Meyer et al. | .................. | 607/9 |
| 2007/0112387 A1 * | 5/2007 | Meyer et al. | .................. | 607/9 |

* cited by examiner

*Primary Examiner*—George Manuel
(74) *Attorney, Agent, or Firm*—Hollingsworth & Funk, LLC (57) ABSTRACT

Systems and methods provide for selection of automatic capture verification modes. A number of capture verification modes are evaluated, wherein at least one of the capture verification modes has a distinct temporal relationship between delivery of a pacing pulse and detection of capture of heart tissue by the pacing pulse than the other capture verification modes. One or more capture verification modes are selected based on the evaluation. Capture verification is implemented using the selected one or more capture verification modes.

18 Claims, 9 Drawing Sheets

SELECTION OF CARDIAC CAPTURE VERIFICATION MODES

FIELD OF THE INVENTION

The present invention relates generally to cardiac rhythm management methods and devices and, more particularly, to selection of one or more capture verification modes.

BACKGROUND OF THE INVENTION

The healthy heart produces regular, synchronized contractions. Rhythmic contractions of the heart are normally controlled by the sinoatrial (SA) node, specialized cells located in the upper right atrium. The SA node is the normal pacemaker of the heart, typically initiating 60-100 heart beats per minute. When the SA node is pacing the heart normally, the heart is said to be in normal sinus rhythm (NSR).

Bradycardia occurs when the heart rhythm is too slow. This condition may be caused, for example, by delayed impulses from the SA node, denoted sick sinus syndrome, or by a blockage of the electrical impulse between the atria and ventricles. Bradycardia produces a heart rate that is too slow to maintain adequate circulation.

Implantable cardiac rhythm management systems, such as pacemakers, have been used as an effective treatment for patients with bradycardia. These systems typically comprise circuitry to sense signals from the heart and a pulse generator for providing electrical pulses to the heart. Leads extending into the patient's heart are connected to electrodes that contact the myocardium for sensing the heart's electrical signals and for delivering pulses to the heart in accordance with various pacing therapies.

Pacemakers deliver low energy electrical pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing the heart. Single chamber pacemakers may pace and sense one heart chamber. A typical single chamber pacemaker is connected to a lead extending either to the right atrium or the right ventricle. Dual chamber pacemakers may pace and sense two chambers of the heart. A typical dual chamber pacemaker is typically connected to two leads, one lead extending to the right atrium and one lead to the right ventricle. Biventricular pacemakers may be used to provide pacing pulses to both the left ventricle and the right ventricle. Biventricular pacing may be particularly advantageous for delivering cardiac resynchronization therapy for patient's suffering from congestive heart failure (CHF).

If a pace pulse produces a contraction or "captures" the heart tissue, an electrical signal associated with the contraction may be detected and used to confirm that capture has occurred. Pace pulses that fail to produce a contraction in the heart tissue result in non-capture. Non-capture may occur when the pacing pulse energy is too low, and/or if the pacing pulse is delivered during a refractory period of the cardiac tissue.

The present invention involves enhanced methods and systems for verifying capture and provides various advantages over the prior art.

SUMMARY OF THE INVENTION

Embodiments of the present invention are directed to methods and systems for implementing selection of automatic capture verification modes. One embodiment involves a method for automatically implementing capture verification in a cardiac rhythm management system. A number of capture verification modes are evaluated. At least one of the capture verification modes has a distinct temporal relationship between delivery of a pacing pulse and detection of capture of heart tissue by the pacing pulse than the other capture verification modes. One or more capture verification modes are selected based on the evaluation. Capture verification is implemented using the selected one or more capture verification modes.

The at least one capture verification mode may comprise a single chamber capture verification mode or may comprise a multi-chamber capture verification mode.

According to various aspects of the invention, the at least one capture verification mode may use the same capture verification algorithm or a different capture verification algorithm than the other capture verification modes. The at least one capture verification mode may use the same sensing vector or a different sensing vector than the other capture verification modes. The at least one capture verification mode may use a sensing vector for detecting capture that is spatially more distal from the pacing vector than a sensing vector used for detecting capture by the other capture verification modes.

In one implementation, the plurality of capture verification modes may be evaluated during a capture threshold test. In another implementation, the plurality of capture verification modes may be evaluated on a beat by beat basis. The evaluation of the capture verification modes may involve sensing for capture using each of the plurality of capture verification modes based on cardiac signals of one cardiac cycle. Alternatively, the evaluation of the capture verification modes may involve sensing for capture using each of the plurality of capture verification modes based on cardiac signals of multiple cardiac cycles.

In some implementations, the one or more capture verification modes may be selected based at least in part on a hierarchy of capture verification modes. In other configurations, the one or more capture verification modes may be selected based at least in part on a temporal proximity of capture detection of the one or more capture verification modes to the timing of the pacing pulse. In further implementations, the one or more capture verification modes may be selected based at least in part on the reliability of capture detection of the selected capture detection mode. If multiple capture detection modes are selected, capture verification may be implemented using a combination of the multiple capture detection modes. For example, a first capture verification mode may be confirmed by a second capture verification mode. The plurality of capture verification modes may be re-evaluated and the selection may be modified. For example, re-evaluation may occur periodically, or upon detection that patient conditions have changed.

Another embodiment of the invention is directed to a cardiac capture verification system. The system includes sensing circuitry configured to sense cardiac response signals to a pacing pulse associated with capture verification modes. Capture detection circuitry is configured to analyze the cardiac response signals to detect capture in accordance with the plurality of capture verification modes. The capture verification modes include at least one capture verification mode of the plurality of capture verification modes having a distinct temporal relationship between delivery of a pacing pulse and detection of capture of heart tissue by the pacing pulse than other capture verification modes of the plurality of capture verification modes. A processor is coupled to the capture detection circuitry. The processor is configured to evaluate the capture verification modes and to select one or more capture verification modes for implementation based on the evaluation.

According to one aspect of the invention, the sensing circuitry includes a first electrode configured to sense a first cardiac response signal used for capture detection in a first capture verification mode and a second electrode configured to sense a second cardiac response signal used for capture detection in a second capture verification mode. The first electrode is spatially more distant from a pacing electrode than the second electrode. In various configurations, one or more of the cardiac response signals may be sensed using a pacing electrode, a defibrillation coil, or other electrode. In various implementations, one or more of the cardiac response signals may comprise a wireless ECG signal, a surface ECG signal, a T-wave signal, or an electrogram signal.

The processor is may be configured to evaluate the plurality of capture verification modes using the plurality of cardiac response signals sensed during one cardiac cycle. Alternatively, the processor may be configured to evaluate the plurality of capture verification modes using the plurality of cardiac response signals sensed during a sequence of cardiac cycles.

According to some aspects, selection of the capture verification modes may be based at least in part on a temporal proximity of capture detection determined by the one or more capture verification modes to the timing of the pacing pulse.

According to another aspect, the capture verification system may include a memory configured to store a hierarchy of capture verification modes. The processor may be configured to select the one or more capture verification modes based at least in part on the stored hierarchy of capture verification modes.

According to a further aspect, the processor may be configured to select the one or more capture verification modes to facilitate backup pacing, to enhance the reliability of capture detection, to support capture verification for multi-chamber pacing, or to provide other features related to capture verification. In some implementations, the processor selects multiple capture verification modes for implementation as a combination.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized in accordance with the invention, and structural and functional changes may be made without departing from the scope of the present invention.

Cardiac rhythm management (CRM) devices such as pacemakers operate to stimulate the heart tissue via implanted electrodes to produce contractions of the heart tissue. Whether an applied electrical pacing stimulus from the implanted electrodes produces a contraction, or "captures" the heart tissue may be determined by evaluating post-pace electrical signals produced by the heart. Automatic capture verification (ACV) refers to the ability of the CRM device to sense whether a delivered pacing pulse stimulates the myocardium. A CRM device may perform ACV by evaluating sensed cardiac signals to determine if capture occurs after a pacing pulse is delivered to the heart.

Various modes for performing ACV have been implemented to verify when pacing stimuli result in cardiac capture. Different ACV technique may use different approaches in order to overcome various technological constraints, allowing for a broad implementation of the ACV feature. Each ACV technique brings with it a different set of implementation requirements, operating constraints, and functionalities, resulting in different ACV techniques being more appropriate than others for different patients, different operating conditions, or different device parameters.

The ability to implement ACV temporally local to the stimulation site is preferred for therapeutic purposes. Temporally local ACV analysis, e.g. within about 80 ms from the time the pacing pulse is delivered, provides the ability to rapidly evaluate the capture status and to provide backup pacing, if necessary. ACV analysis that is temporally more distal from the time of pacing, e.g., greater than about 100 ms from the time the pacing pulse is delivered, requires a longer time window to evaluate the capture status, relegating these approaches to a more diagnostic role. In general, the local ACV implementations are more sensitive to local electrophysiological phenomena, such as lead polarization, virtual electrode effects, and other phenomena, whereas the temporally distal approaches are in general more immune to such phenomena, and thus more robust.

Embodiments of the present invention describe a method by which multiple ACV modes may be integrated to enhance the device functionality tailored to the needs of an individual patient. The ACV modes provided by the device may be evaluated serially or in parallel and one or more of the available ACV modes are selected and implemented for capture verification. For example, the ACV modes may be evaluated based on their ability to provide reliable capture detection, fusion response, noise immunity, ability to support multi-chamber/multi-site pacing, ability to support different lead types, ability to provide ACV during and after mode switch operations, whether or not the patient needs frequent or less frequent pacing energy adjustments, and/or other factors. Combining multiple ACV modes may be used to provide a hybrid ACV methodology. If more than one ACV mode is selected, the more temporally distal ACV mode or modes may be used to confirm the more temporally local ACV mode or modes which are more sensitive to local phenomena. The evaluation and selection of ACV modes allows a device to dynamically alter its ACV approach to deliver enhanced diagnostic and therapeutic functionality to the patient, without substantially reducing the level of patient safety.

In accordance with embodiments of the invention, capture verification is implemented through the evaluation and selection of one or more suitable ACV modes. More specifically, an implantable CRM device may execute processes for evaluating post-pace electrical signals produced by the heart during a capture threshold procedure and/or on a beat by beat basis. The CRM device selects the most appropriate ACV mode the patient can support based on the evaluation. Selection of the ACV mode may be based on a preferred hierarchy of ACV modes. The preferred hierarchy may involve a default hierarchy stored in the device memory and/or may involve a hierarchy that has been input or modified by a physician or other person. In many situations, the more preferred ACV modes are modes that provide capture detection more temporally local to the timing of the pacing pulse because of the increased therapeutic value of the more temporally local modes.

The use of different ACV modes that are selectably implementable make capture verification technology extensible to the broadest possible patient population. As previously discussed, each ACV mode brings with it different implementation requirements, operating constraints, and functionality, and different approaches may be more appropriate for different patients. ACV mode selection illustrated in the embodiments described herein allows the device to evaluate multiple different ACV modes to determine an appropriate ACV implementation for a particular patient at a particular point in time. ACV mode selection allows the CRM system to compensate for technological constraints specific to particular capture detection implementations, such as the evoked response sensing characteristics of pacing and defibrillation electrodes, multi-chamber capture detection, and/or other capture detection characteristics. ACV mode selection methodologies as described herein may be advantageously deployed in implantable devices having multiple ACV modes available for operation in the same region of the heart. The ACV mode evaluation and selection methodologies described in the exemplary embodiments allow the device to dynamically alter its ACV approach to deliver enhanced diagnostic and/or therapeutic functionality to the patient, without reducing the level of patient safety.

Figure 1:
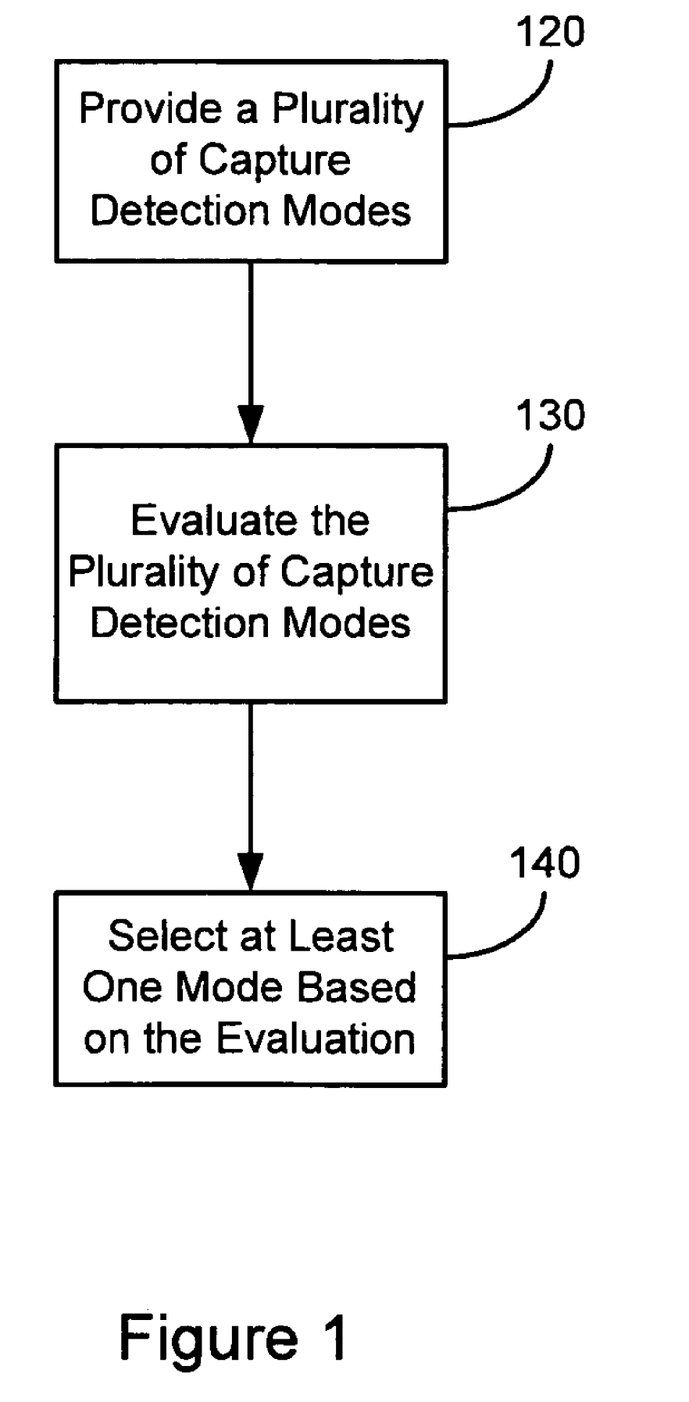
FIG. 1 is a flowchart illustrating a method for implementing capture verification accordance with embodiments of the invention.

FIG. 1 illustrates a method of implementing capture verification in accordance with embodiments of the invention. The CRM system provides 120 a plurality of ACV modes that are respectively associated with a plurality of processes for detecting capture of heart tissue by a pacing pulse. The timing of capture detection for each ACV mode has a distinct temporal relationship with respect to the timing of the pacing pulse. For example, some ACV modes may rely on detection of cardiac signal features occurring closer in time to the delivery of the pacing pulse than other cardiac signal features used for other ACV modes. The ACV modes are evaluated 130. In various embodiments, the ACV modes may be evaluated during capture threshold testing, and/or on a beat by beat basis. One or more ACV modes are selected 140 for implementation. The selection of ACV modes may involve identifying one or more ACV modes that are consistent with the needs of the patient and/or the operating parameters of the device. If more than one ACV mode is selected, the selected ACV modes may be implemented in combination or may be implemented individually based on the presence of different patient and/or device conditions.

Following implementation, the available ACV modes may be re-evaluated and the previous ACV mode selection may be changed to allow the device to adapt to changing patient and/or device conditions. For example, the ACV modes may be re-evaluated periodically, e.g., nightly or according to some other pre-established schedule. Further, a physician may manually request ACV mode evaluation via a remote communication session or during an office visit. In other implementations, an AVC mode re-evaluation may be triggered following detection of an event, such as a loss of capture event, a mode switch, pacing rate change, tachy therapy delivery, thoracic impedance change, blood pressure change, weight change, and/or other event that may alter the effectiveness of capture verification.

According to one implementation, evaluation of the ACV modes may be performed during a single cardiac beat, or during multiple cardiac beats during capture threshold testing. After performing a capture threshold test including ACV mode evaluation, the device may select one or more ACV modes for implementation. In another implementation, the device may evaluate ACV modes on a beat to beat basis and dynamically switch between ACV modes.

As previously discussed, capture detection used for the various ACV modes involves evaluating cardiac response signals following a delivered pacing pulse to determine if the pacing pulse captured the heart tissue. For different ACV modes, the sensing vectors used to sense the cardiac signals may include electrodes that have differing spatial distances from the pacing electrode and/or differing temporal distances from the timing of the pacing pulse. In general, but not always, ACV modes using sensing electrodes located at a greater spatial distance from the pacing electrode take a longer time to determine whether the pacing pulse captured the heart tissue when compared to ACV modes using sensing electrodes that are located spatially closer to the pacing electrode. In other words, the temporal distance of capture detection relative to the timing of the pacing pulse may increase with the spatial distance of the sensing electrode relative to the pacing electrode. ACV modes using more distally located sensing electrodes may take longer to detect capture due to the delay in the arrival of the depolarization wavefront at sensing electrodes that are remote from the pacing electrode.

The signal features used for capture detection in different ACV modes may occur at different times with respect to the timing of the pacing pulse. In general, ACV modes that rely on signal features that occur at greater temporal distance from the timing of the pacing pulse take longer to detect capture than ACV modes that use signal features that occur closer in time to the timing of the pacing pulse.

ACV modes evaluated in accordance with embodiments of the invention may involve sensing cardiac signals for capture detection using intracardiac or intra-thoracic electrodes placed in, on, or near the heart or the cardiac vasculature and/or subcutaneous, non-intra-thoracic electrodes disposed under the skin of the patient, but outside the thoracic cavity, such as electrodes disposed on the housing of an implantable device, and/or patient-external electrodes positioned on or near the surface of the patient's body.

In various examples, the ACV modes available for selection by a CRM device may include beat to beat capture detection for a single cardiac chamber, periodic single chamber automatic threshold testing, capture verification via T-wave analysis, periodic multi-chamber automatic threshold testing, capture verification via wireless electrocardiogram (ECG) signal analysis, capture verification via analysis of a surface ECG signal, as well as other ACV modes. The cardiac response signal may be an externally sensed signal, such as the surface ECG, or may be an implantably sensed signal, such as a cardiac electrogram. Embodiments of the invention are described in terms of ACV modes as applied to the right ventricle, although the techniques described herein are not limited to right ventricular implementations and may be applied to any heart chamber. The ACV modes discussed herein provide an exemplary set of ACV modes that may be available for evaluation and selection in accordance with the embodiments of the invention. Other ACV modes, or additional ACV modes, may alternatively be evaluated and selected using the processes described herein.

Figure 2:
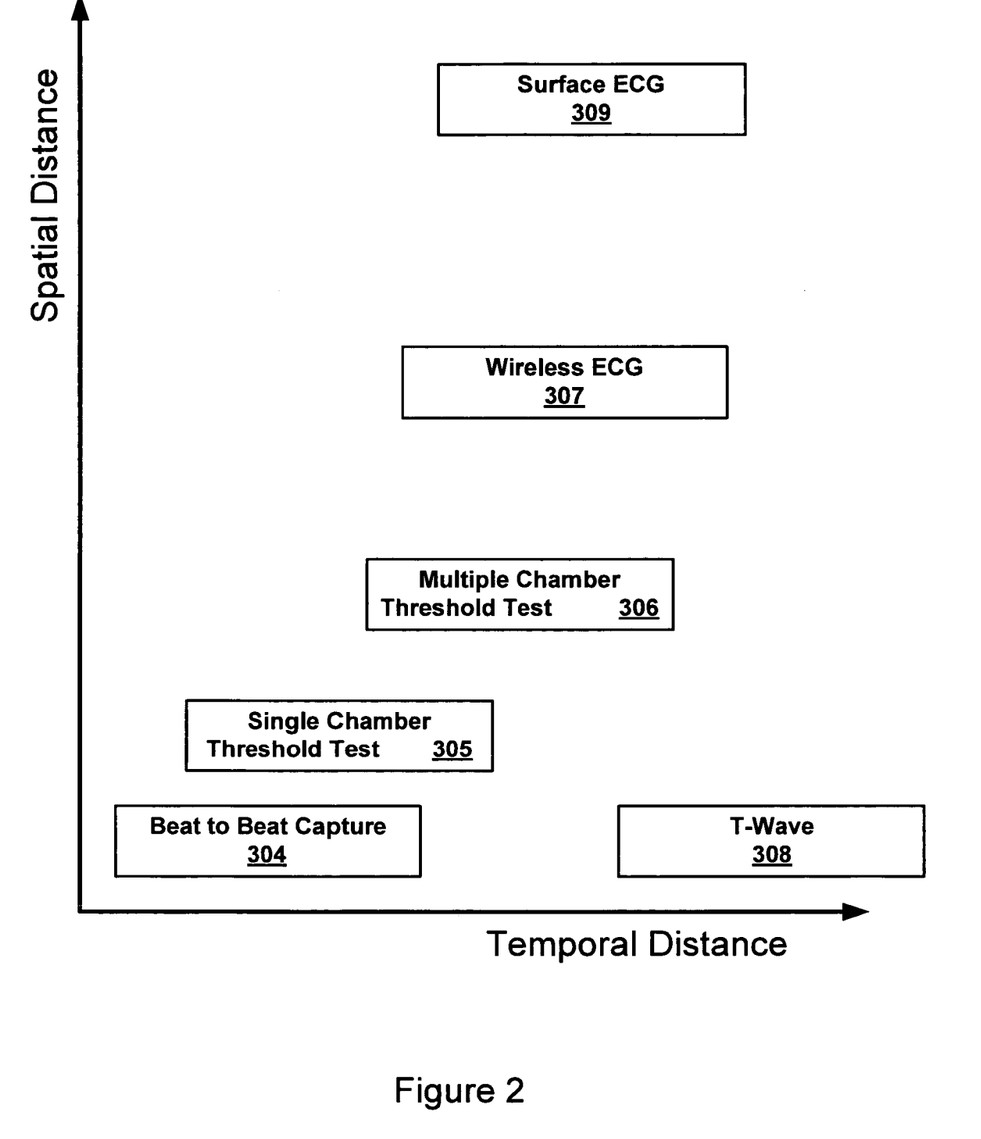
FIG. 2 is a diagram illustrating temporal and spatial relationships of capture detection and sensing electrodes used in selectably implementable capture verification modes in accordance with embodiments of the invention.

FIG. 2 illustrates ACV modes described above as applied to capture verification for the right ventricle (RV) in accordance with one embodiment. In FIG. 2, the X axis represents temporal distance from the stimulation time and the Y axis represents spatial distance from the stimulation site. In this implementation, the ACV modes 304-309 available for evaluation and selection include beat to beat RV capture detection 304, RV threshold testing 305, bi-ventricular threshold testing 306, RV capture detection via wireless ECG 307, T-wave analysis for RV capture detection 308, and RV capture detection via surface ECG 309. FIG. 2 illustrates spatial distances between sensing and pacing electrodes and temporal distances between pacing and capture detection for the different ACV modes 304-309.

As illustrated in FIG. 2, the sensing vector for the beat to beat RV capture ACV mode 304 is spatially relatively close to the pacing vector or may include the pacing vector. For example, pacing may be delivered on the right ventricular (RV) tip electrode to RVring vector and the sensing vector for beat to beat capture detection may include the RV tip to Can sensing vector. The delay in sensing the depolarization wavefront associated with capture is relatively small, e.g., within about 70 ms, and the cardiac signal features used for capture detection occur relatively soon after delivery of the pacing pulse.

Another ACV mode that may be selected in accordance with the processes described herein is the RV threshold testing mode 305. In one embodiment, the RV threshold testing mode 305 employs the RV defibrillation coil for sensing the cardiac pacing response to the delivered pacing pulse. Because the defibrillation coil is located at a greater spatial distance from the pacing electrode than the sensing electrode used for beat to beat capture detection, there is a larger sensing delay in sensing the captured response with the defibrillation coil relative to the sensing delay for the beat to beat capture ACV mode.

Yet another ACV mode illustrated in FIG. 2 involves bi-ventricular pacing with RV or bi-ventricular capture detection 306. RV or bi-ventricular capture detection may include sensing for capture of the right ventricle or both the right and left ventricles after bi-ventricular pacing, wherein an interventricular pacing delay (IVD) occurs between pacing the right and left ventricles. In some scenarios, for example, the interventricular pacing delay (IVD) may be up to about 200 ms. The time required to evaluate the cardiac signal for capture of the left ventricle, right ventricle and/or both ventricles may extend to about 100-200 ms following delivery of biventricular pacing. One example of the bi-ventricular ACV mode 306 involves RV or bi-ventricular capture threshold testing implementing detection of capture for the RV or both ventricles with capture sensing in the RV only. When capture of both ventricles is detected, timing of capture detection may be affected by the spatial distance between the sensing electrode and the pacing electrode of the last paced ventricle, as well as by the duration of the interventricular delay.

Another ACV mode 308 that may be used for verification of RV capture involves sensing the T-wave following delivery of a pacing pulse. In some implementations, RV threshold testing may be accomplished based on detecting a difference in the timing between delivery of the pacing pulse and the occurrence of the T-wave for captured and non-captured beats. Other implementations provide capture detection based on a change in the morphology of the T-wave, such as a change in the T-wave slope.

Some ACV modes illustrated in FIG. 2 involve detecting RV capture by analyzing wireless 307 or surface 309 ECG signals. These ACV modes 307, 309 use cardiac signals sensed using electrodes that are increasingly spatially distant from the pacing electrode. Wireless ECG signals may be sensed, for example, using an indifferent electrode deployed on the subcutaneously implantable housing or header of the CRM device. Surface ECG signals are sensed using patient-external electrodes placed on the surface of the patient's body. These modes provide diagnostic information and exemplify global capture verification modes that are not generally used in therapy applications requiring capture detection for implementation of back up pacing.

Figure 3:
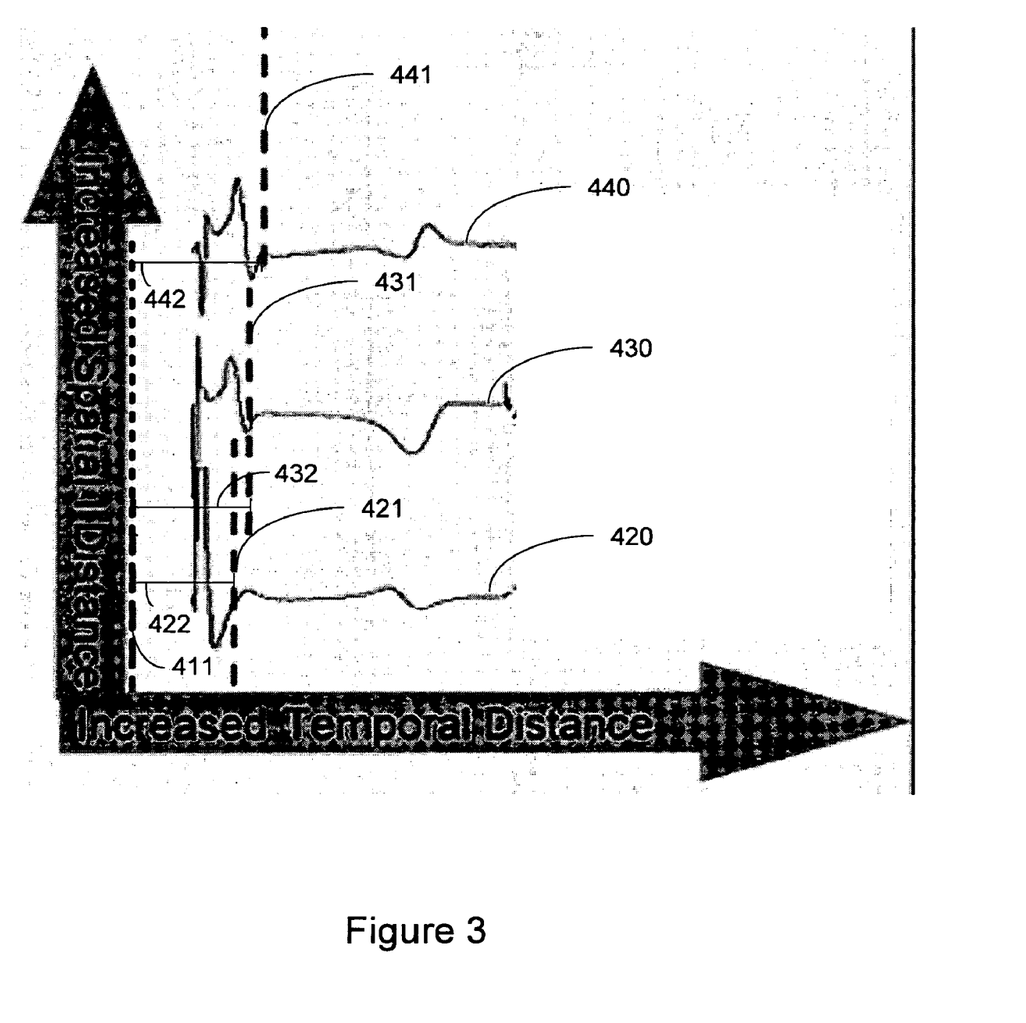
FIG. 3 illustrates the temporal relationship between cardiac signal features used for capture detection in various capture verification modes that may be selected for implementation in accordance with embodiments of the invention.

FIG. 3 illustrates cardiac response signals used for capture detection in three of the ACV modes described in connection with FIG. 2: The cardiac response signals illustrated in FIG. 3 include the cardiac response signal 420 used for beat to beat RV capture detection, the cardiac response signal 430 used in RV automatic threshold testing, and the cardiac response signal 440 used for capture detection via surface ECG, respectively. FIG. 3 illustrates the temporal distances 422, 432, 442 between the cardiac signal features 421, 431, 441 used for capture detection and the pacing pulse 411. As previously discussed, the cardiac signal features 421 used for capture detection in the beat to beat RV capture AVC mode have a relatively small temporal distance 422 relative to the time 411 the pacing pulse is delivered, the cardiac signal features 431 used for capture detection in RV threshold testing ACV mode have a larger temporal distance 432 relative to the time 411 of the delivery of the pacing pulse, and the cardiac signal features 441 used for capture detection in the ACV mode employing a surface ECG have the largest temporal distance 442 relative to the time of the delivery of the pacing pulse.

Figure 4:
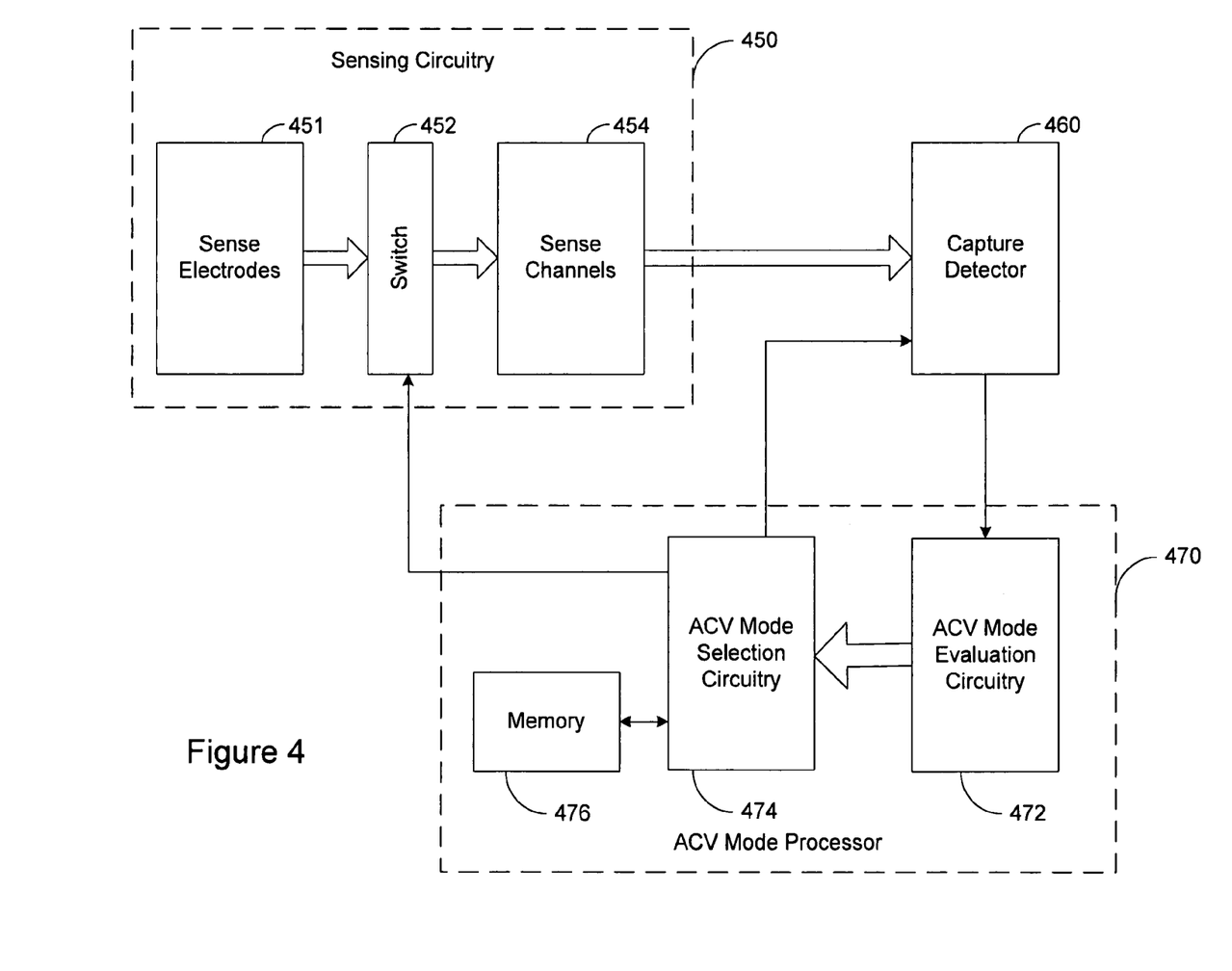
FIG. 4 is a block diagram of a system for selectively implementing one or more capture verification modes in accordance with embodiments of the invention.

FIG. 4 is a block diagram of system for implementing capture verification in a CRM device in accordance with embodiments of the invention. The system includes sensing circuitry 450 comprising a plurality of sense electrodes 451 used for sensing cardiac response signals to pacing. As previously discussed, the sense electrodes 451 may include intracardiac, intra-thoracic, subcutaneous, and/or patient external electrodes. The sense electrodes 451 are coupled to the sensing channels 454, which may include hardware, software and/or firmware components, via a multiplexer switch 452. The sense channels are coupled to the capture detection circuitry 460.

Evaluation of multiple ACV modes may be performed during a single beat or during a series of beats. In one implementation, the multiplexer switch 452 may be operable to couple various pairs of the sense electrodes 451 to various sensing channels 454 in parallel to facilitate evaluation of multiple ACV modes during a single cardiac beat. In another implementation, testing a single ACV mode per beat may be accomplished by coupling a single electrode pair 451 to a single sense channel 454 for the duration of the beat. The electrode pair/sense channel combination may be switched between beats to employ various electrode pair/sense channel combinations until all ACV modes have been tested. Alternatively, the electrode pair/sense channel combination may be switched during a cardiac beat so that more than one ACV mode is tested during the beat.

The capture detection circuitry 460 may include hardware, software, and/or firmware used for implementation of algorithms for detecting capture. In this configuration, the selectable connection between the sense electrodes 451 and the sense channels 454 is controlled by the ACV mode selection circuitry 474 of the ACV mode processor 460. In addition to controlling the connections between sense electrodes 451 and sense channels 454, the mode selection circuitry 474 may also control operation of the capture detector 460 with respect to the circuitry and/or algorithms used for capture detection in conjunction with the particular sense electrodes/sense channels 451, 454 employed.

The capture detector 460 is coupled to the ACV mode evaluation circuitry 472 and provides information to the ACV mode evaluation circuitry and to other components of the CRM device. The capture information is used in the evaluation of various ACV modes in accordance with embodiments of the invention.

Selection of one or more ACV modes based on the evaluation of the ACV modes may be performed in view of a hierarchy of preferred ACV modes stored in memory 476 and accessible by the ACV mode selection circuitry 474. For example, ACV modes that are "faster," taking a relatively shorter time from the time of pacing to verify capture, may be preferred over ACV modes that are "slower," taking a relatively longer time from the time of pacing to verify capture. In some implementations, ACV mode selection may involve more than one ACV mode. The selected ACV modes may be used in combination, and/or may be used at different times and/or under different conditions. In some implementations, a relatively "fast" ACV mode may be used to make the initial capture determination. A relatively "slow" ACV mode may be used to confirm the initial capture determination.

Figure 5:
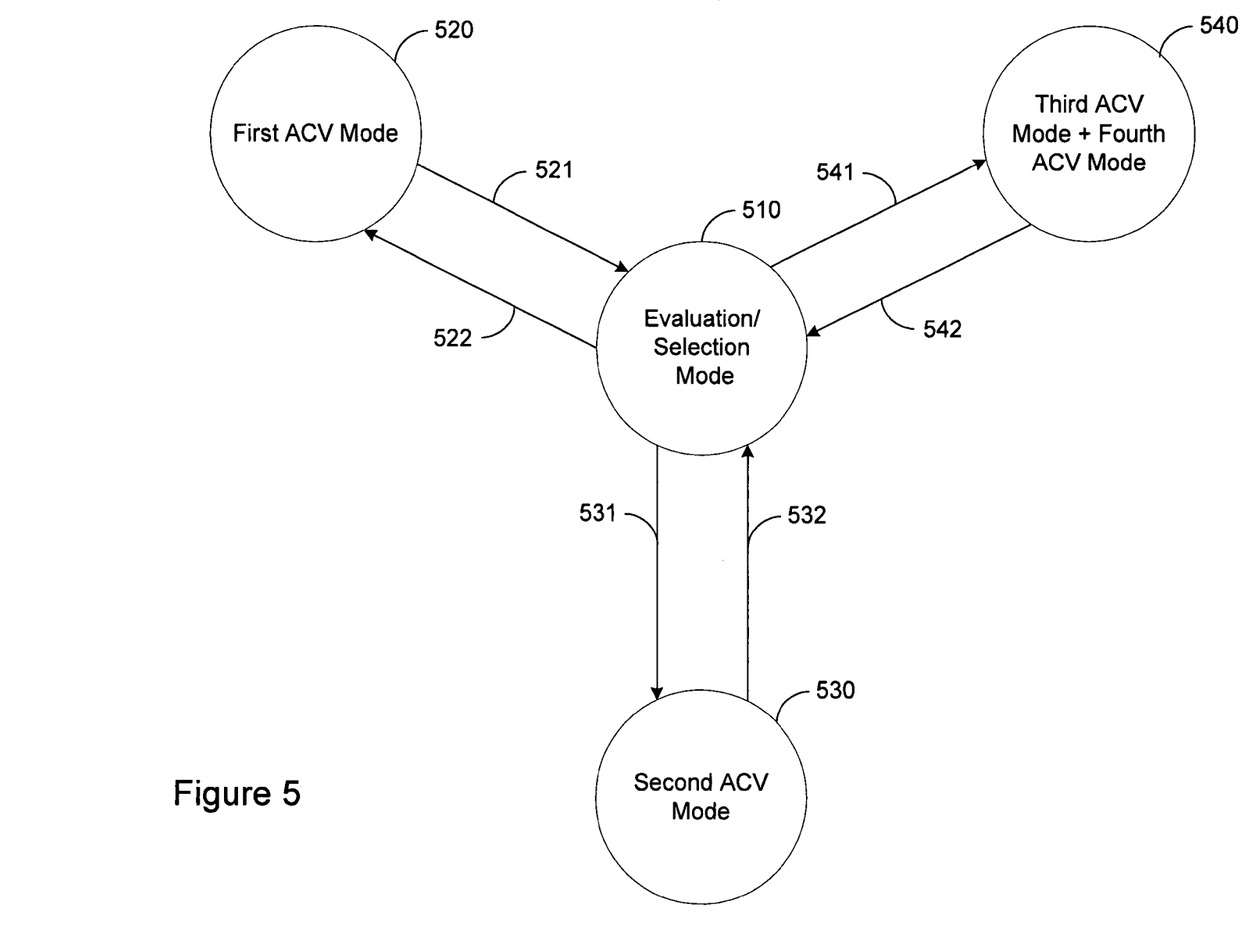
FIG. 5 is a diagram conceptually illustrating selection of capture verification modes in accordance with embodiments of the invention.

FIG. 5 is a conceptual diagram illustrating operation of the ACV mode selection process in accordance with embodiments of the invention. Initially, the system implements capture verification using a first ACV mode 520. Periodically, the system evaluates the available ACV modes and selects one or more of the ACV modes. To evaluate the available ACV modes, the system enters an evaluation/selection mode 510, which may involve performing capture threshold testing or may involve beat to beat evaluation, to evaluate one or more of the ACV modes. In one embodiment, all of the available ACV modes are tested during each paced cycle of the evaluation period. In another embodiment, the ACV modes are tested during a series of paced cycles, with one ACV mode tested during a cardiac cycle. In other embodiments, greater than one ACV mode, but less than all ACV modes are tested during a cardiac cycle of the evaluation period.

As illustrated in FIG. 5, after implementing capture verification using the first ACV mode 520 for a period of time, the system transitions 521 to evaluation/selection mode 510. During the evaluation/selection mode 510, the system tests and evaluates the available ACV modes. Following the evaluation, one or more of the ACV modes may be selected to implement capture verification. In the example provided in FIG. 5, the system selects a second ACV mode 530 and transitions 531 to the second ACV mode 530. In some scenarios, the system may have selected a transition 522 back to the first ACV mode 520, or a transition 541 to a combination of third and fourth ACV modes 540. Capture verification is implemented according to the second ACV mode 530 for a period of time. Periodically, the system may transition 532 into evaluation/selection mode 510 to test the continued appropriateness of the second ACV mode 530. If the second ACV mode 530 is selected again after testing, then the system transitions 531 back into the second ACV mode 530. Eventually, the system may transition to 522, 541 another mode or modes for capture verification. For example, after testing, the system may determine that capture verification using a combination of third and fourth ACV modes 540 is most appropriate. If so, the system transitions 541 to a state wherein third and fourth ACV modes 540 are used for capture verification. The system may transition 542 from the combination mode 540 and into 521, 531 other modes 520, 530 as appropriate.

Figure 6:
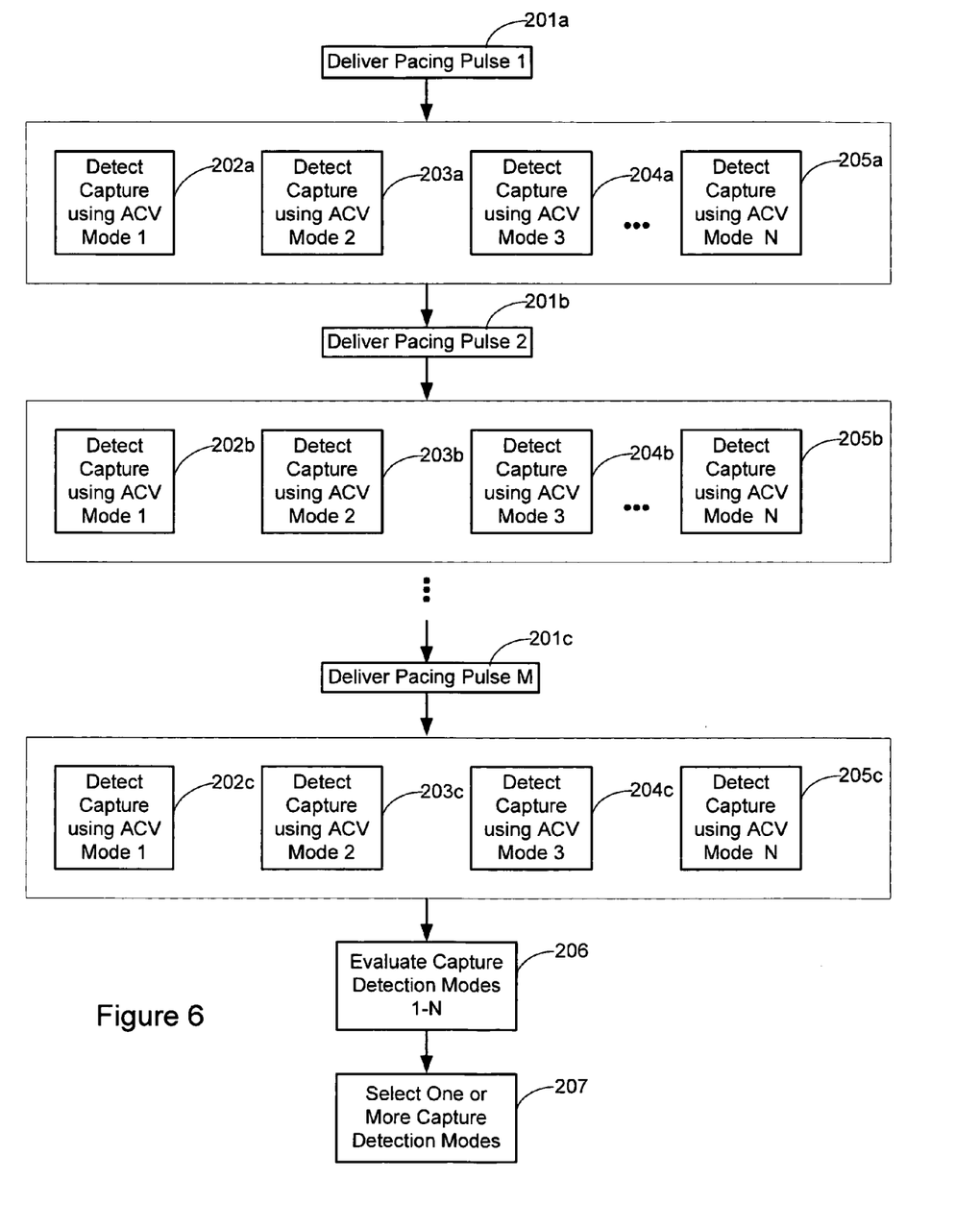
FIGS. 6 and 7 are flowcharts illustrating single beat and multiple beat ACV mode evaluation, respectively, in accordance with embodiments of the invention.
Figure 7:
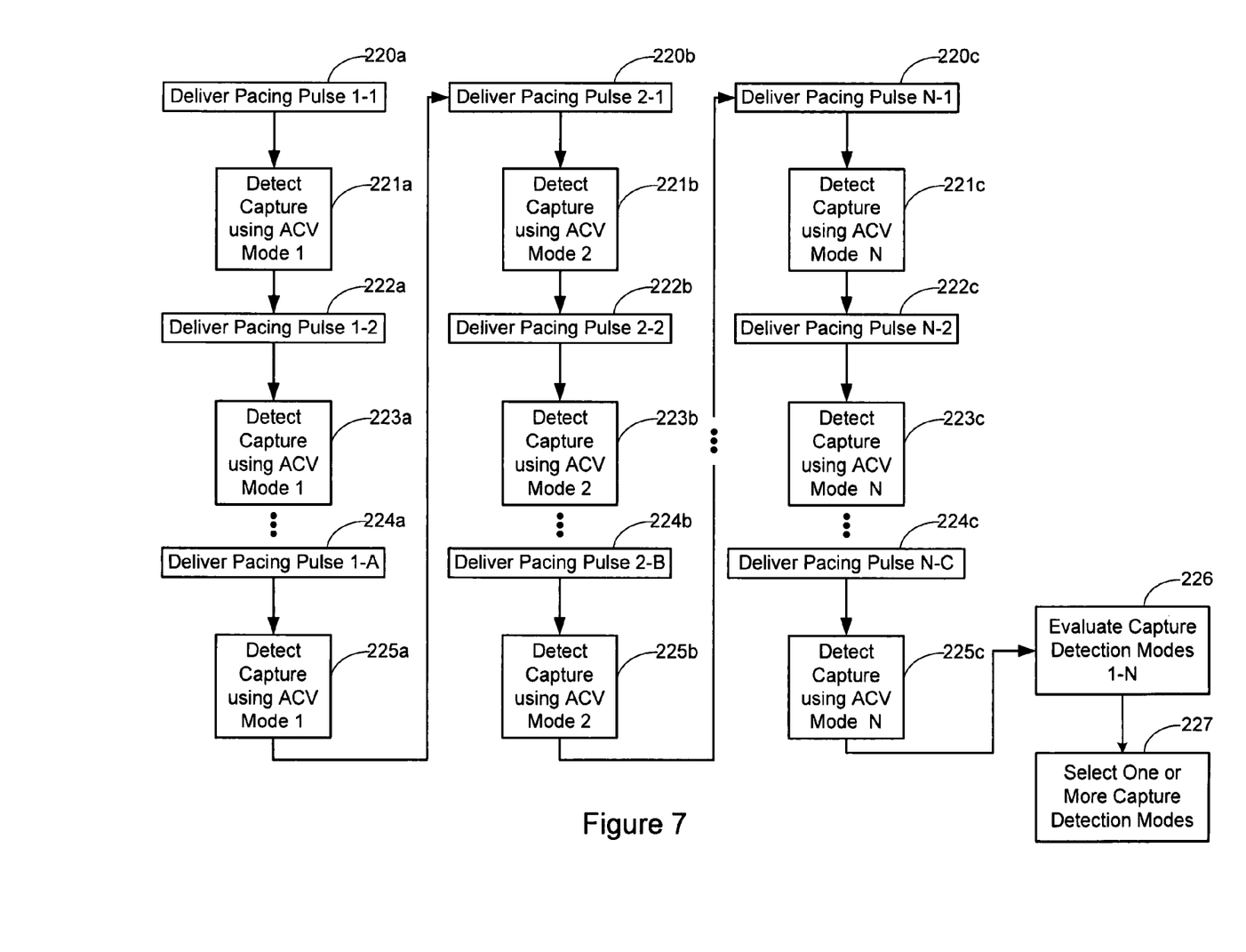

FIGS. 6 and 7 illustrate single beat and multiple beat ACV mode evaluation, respectively, in accordance with embodiments of the invention. Single beat and/or multiple beat ACV mode testing may occur during the evaluation process. In single beat ACV mode testing, illustrated in FIG. 6, more than one ACV mode is tested during each cardiac cycle of the evaluation period. In one implementation, single beat ACV mode testing may be performed using parallel connections between sense electrodes and sensing channels. In another implementation, the different methods could be evaluated sequentially, by testing the response on a beat by beat basis.

A parallel implementation of single beat ACV mode testing is illustrated in FIG. 6. Pacing pulses 1-M are delivered 201a, 201b, 201c during the test. After delivery of each pacing pulse 201a, 201b, 201c, capture is detected using ACV modes 1-N. In the example provided in FIG. 6, during each 1-M paced cycle, capture is detected using a first ACV mode 202a, 202b, 202c, a second ACV mode 203a, 203b, 203c, a third ACV mode 204a, 204b, 204c, and continuing to an Nth ACV mode 205a, 205b, 205c. For example, the system may detect capture using the sense vectors and processes used for beat to beat RV capture, using the sense vectors and processes used for RV threshold testing, using the sense vectors and processes used for bi-ventricular capture detection, using the sense vectors and processes used for wireless ECG, using the sense vectors and processes used for surface ECG, and using the sense vectors and processes used for T-wave analysis. During testing, a fastest ACV mode may be performed first, with slower ACV modes performed later based on their temporal distance from the timing of the pacing pulse.

After 1-N ACV modes have been tested during 1-M paced cardiac cycles, the ACV modes are evaluated 206 and one or more of the ACV modes are selected 207 for implementation. As previously discussed, in some embodiments, the selection may be based on a pre-established hierarchy of preferred ACV modes. The preferred hierarchy may take into account patient conditions, device conditions, history of success of particular ACV modes, and/or other factors in making the ACV mode selection.

FIG. 7 illustrates sequential testing of ACV modes during capture threshold testing. During sequential testing, a single ACV mode is tested during a paced cardiac cycle. As illustrated in FIG. 6, ACV mode 1 is tested during A paced cycles, ACV mode 2 is tested during B paced cycles, and ACV mode N is tested during C paced cycles. Capture is detected using the first ACV mode 221*a*, 223*a*, 225*a* following delivery of pacing pulses 1-1 through 1-A 220*a*, 222*a*, 224*a*. Capture is detected using the second ACV mode 221*b*, 223*b*, 225*b* following delivery of pacing pulses 2-1 through 2-B 220*b*, 222*b*, 224*b*. Capture is detected using the Nth ACV mode 221*c*, 223*c*, 225*c* following delivery of pacing pulses N-1 through N-C 220*c*, 222*c*, 224*c*. After ACV modes 1-N have been tested during the paced cardiac cycles, the ACV modes are evaluated 226 and one or more of the ACV modes are selected 227 for implementation.

Figure 8:
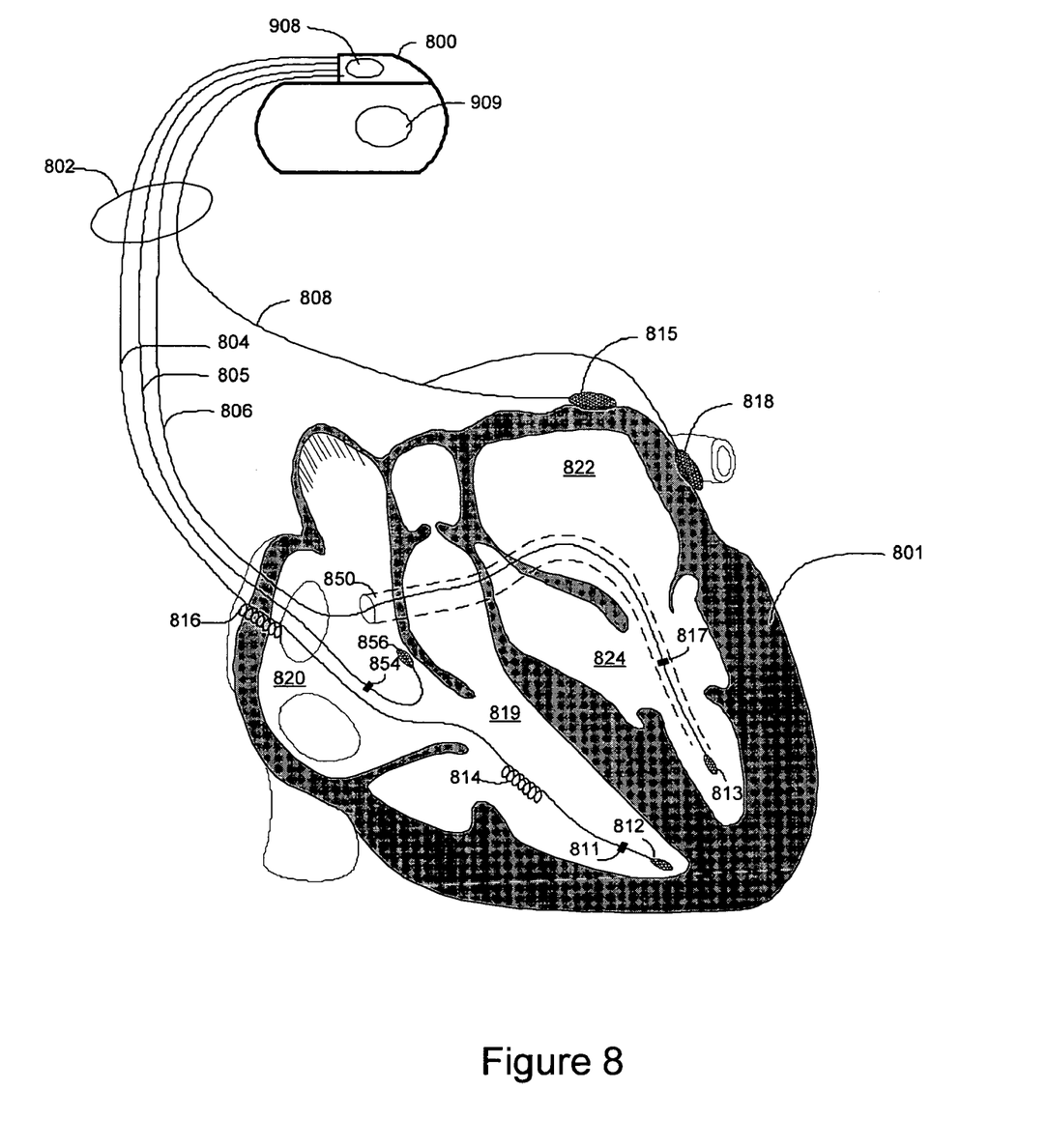
FIG. 8 is a partial view of one embodiment of an implantable cardiac rhythm management device capable of implementing capture verification processes in accordance with embodiments of the invention.

Referring now to FIG. 8 of the drawings, there is shown an implantable CRM system that may be used to implement the above described selection of ACV modes according to the present invention. The CRM system in FIG. 8 includes a pacemaker/defibrillator (PD) 800 electrically and physically coupled to a lead system 802. A capture detector and ACV mode processor described in connection with FIG. 4, and elsewhere herein, may be disposed within the housing of the PD 800 along with sensing, control and therapy circuitry. The housing and/or header of the PD 800 may incorporate one or more electrodes 908, 909 used to provide electrical stimulation energy to the heart and/or to sense cardiac electrical activity. The PD 800 may utilize all or a portion of the PD housing as a can electrode 909. The PD 800 may include an indifferent electrode positioned, for example, on the header or the housing of the PD 800. If the PD 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 8, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 8 illustrates one embodiment that may be used in connection with the ACV mode selection methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 8, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 8 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the ICD 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to effect bipolar pacing and/or sensing.

FIG. 8 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 9:
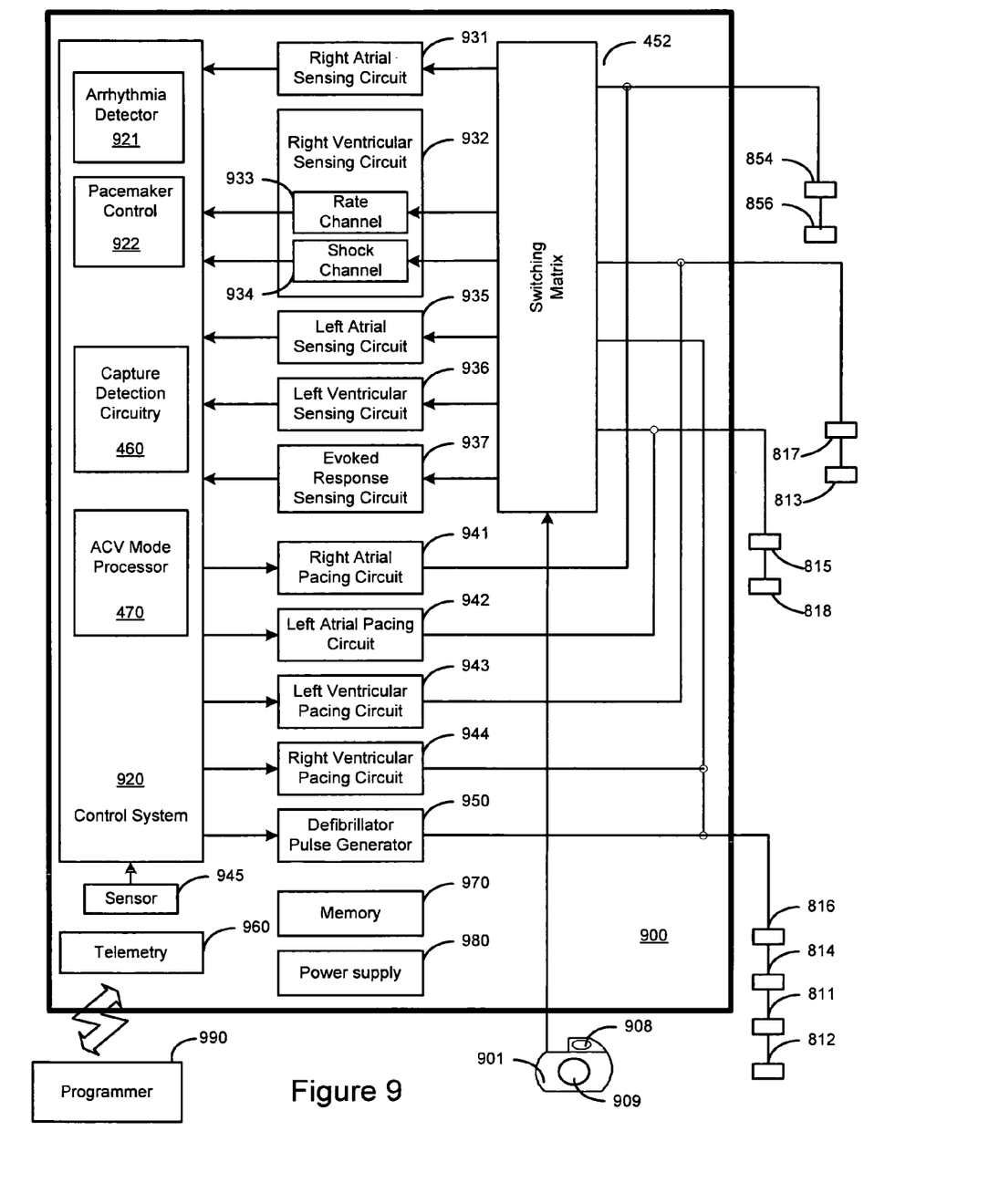
FIG. 9 is a block diagram of cardiac rhythm management device that may be used to implement capture verification in accordance with embodiments of the invention.

Referring now to FIG. 9, there is shown an embodiment of a cardiac pacemaker/defibrillator (PD) 900 suitable for implementing a capture verification method evaluation and selection methodologies for a variety of capture verification methods according to the present invention. FIG. 9 shows a PD 900 divided into functional blocks. It is understood by those skilled in the art that there exist many possible configurations in which these functional blocks can be arranged. The example depicted in FIG. 9 is one possible functional arrangement. Other arrangements are also possible. For example, more, fewer or different functional blocks may be used to describe a cardiac defibrillator suitable for implementing the methodologies for verifying capture using a number of capture verification methods in accordance with methods of the present invention. In addition, although the PD 900 depicted in FIG. 9 contemplates the use of a programmable microprocessor-based logic circuit, other circuit implementations may be utilized.

The PD 900 depicted in FIG. 9 includes circuitry for receiving cardiac signals from a heart and delivering electrical stimulation energy to the heart in the form of pacing pulses or defibrillation shocks. In one embodiment, the circuitry of the PD 900 is encased and hermetically sealed in a housing 901 suitable for implanting in a human body. Power to the PD 900 is supplied by an electrochemical battery 980. A connector block (not shown) is attached to the housing 901 of the PD 900 to allow for the physical and electrical attachment of the lead system conductors to the circuitry of the PD 900.

The PD 900 may be a programmable microprocessor-based system, including a control system 920 and a memory 970. The memory 970 may store information associated with ACV mode selection, including a stored hierarchy of preferred ACV modes, along with other information. The historical data storage may include data obtained from long term patient monitoring and may be used to develop a historical evaluation of the success of various ACV modes. Stored data, as well as other information, may be transmitted to an external programmer unit 990 as needed or desired.

The control system 920 and memory 970 may cooperate with other components of the PD 900 to control the operations of the PD 900. The control system depicted in FIG. 9 incorporates a capture detector 460 for detecting capture and an ACV mode processor 470 for evaluating a variety of ACV modes and selecting one or more of the ACV modes in accordance with various embodiments of the present invention. The control system 920 may include additional functional components including a pacemaker control circuit 922, an arrhythmia detector 921, and a template processor for cardiac signal morphology analysis, along with other components for controlling the operations of the PD 900.

Telemetry circuitry 960 may be implemented to provide communications between the PD 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the PD 900 from the programmer unit 990 during and after implant. In addition, stored cardiac data pertaining to capture threshold, capture detection and/or cardiac response classification, for example, along with other data, may be transferred to the programmer unit 990 from the PD 900.

In the embodiment of the PD 900 illustrated in FIG. 9, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals. A bipolar RV signal may be sensed as a voltage developed between the RV-tip 812 and the RV-ring 811. Alternatively, bipolar sensing in the right ventricle may be implemented using the RV-tip electrode 812 and the RV-coil 814. Unipolar sensing in the right ventricle may be implemented, for example, by sensing voltages developed between the RV-tip 812 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Outputs from the right ventricular sensing circuit 932 are coupled to the control system 920. In one embodiment of the invention, rate channel signals and shock channel signals may be used to develop morphology templates for analyzing cardiac signals. In this embodiment, rate channel signals and shock channel signals may be transferred from the right ventricular sensing circuit 932 to the control system 920 and to a template processor where the morphological characteristics of a cardiac signal are analyzed for capture detection.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 to the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936.

The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to various sensing circuits 931-936. An evoked response sensing circuit 937 may be used to sense and amplify voltages developed using various combinations of electrodes. An evoked response sensing circuit 937 may be used to sense cardiac signals indicative of a cardiac response to pacing, e.g., capture or non-capture. Cardiac signals indicative of the cardiac pacing response may be sensed and amplified by the evoked response circuit 937 and may be analyzed by a capture detector to determine cardiac pacing response.

The PD 900 may incorporate one or more metabolic sensors 945 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need.

The ability to evaluate multiple ACV modes and to dynamically switch between ACV modes allows ACV implementation to react and adapt to changing patient conditions. Furthermore, selection of ACV modes allows ACV to be implemented for a broad patient population. The ACV mode selection approaches described herein allow CRM devices to evaluate multiple ACV modes and to select a most appropriate ACV implementation that a patient can support, while reducing the physician time required to optimize therapy or diagnostics based on ACV mode.

Various modifications and additions may be made to the embodiments discussed herein without departing from the scope of the present invention. Accordingly, the scope of the present invention should not be limited by the particular embodiments described above, but should be defined only by the claims set forth below and equivalents thereof.

What is claimed is:

1. A method for automatically implementing capture verification in a cardiac rhythm management system, comprising:
    evaluating a plurality of capture verification modes used to operate the cardiac rhythm management system to verify capture, at least one capture verification mode of the plurality of capture verification modes having a temporal relationship between delivery of a pacing pulse and detection of capture of heart tissue by the pacing pulse that is different from another capture verification mode of the plurality of capture verification modes;
    selecting one or more capture verification modes based on the evaluation of the plurality of capture verification modes, including selecting based on a time interval duration of each of the one or more capture verification modes, the time interval duration measured between a given pacing pulse and a cardiac signal feature used for capture detection for such pacing pulse; and
    implementing capture verification using the selected one or more capture verification modes.

2. The method of claim 1, wherein the at least one capture verification mode comprises a single chamber capture verification mode.

3. The method of claim 1, wherein the at least one capture verification mode comprises a multi-chamber capture verification mode.

4. The method of claim 1, wherein the at least one capture verification mode uses a different capture detection algorithm or a different sensing vector than the another capture verification mode.

5. The method of claim 1, wherein the at least one capture verification mode uses a same sensing vector for detecting capture as the another capture verification mode.

6. The method of claim 1, wherein the at least one capture verification mode uses a same capture detection algorithm for detecting capture as the another capture verification mode.

7. The method of claim 1, wherein the at least one capture verification mode uses a sensing vector for detecting capture that is spatially more distal from the pacing vector than a sensing vector used for detecting capture by the another capture verification mode.

8. The method of claim 1, wherein evaluating the plurality of capture verification modes comprises evaluating the plurality of capture verification modes during a capture threshold test.

9. The method of claim 1, wherein evaluating the plurality of capture verification modes comprises evaluating the plurality of capture verification modes on a beat by beat basis.

10. The method of claim 1, wherein evaluating the plurality of capture verification modes comprises sensing for capture using each of the plurality of capture verification modes based on cardiac signals of one cardiac cycle.

11. The method of claim 1, wherein evaluating the plurality of capture verification modes comprises sensing for capture using each of the plurality of capture verification modes based on cardiac signals of multiple cardiac cycles.

12. The method of claim 1, wherein selecting the one or more capture verification modes comprises selecting the one or more capture verification modes based at least in part on capture detection reliability of the selected one or more capture verification modes.

13. The method of claim 1, wherein selecting the one or more capture verification modes comprises selecting the one or more capture verification modes based at least in part on a hierarchy of capture verification modes.

14. The method of claim 1, wherein selecting the one or more capture verification modes comprises selecting the one or more capture verification modes based at least in part on a temporal proximity of capture detection of the one or more capture verification modes to the timing of the pacing pulse.

15. The method of claim 1, wherein:
    selecting the one or more capture verification modes comprises selecting multiple capture verification modes; and
    implementing capture verification comprises implementing capture verification using a combination of the multiple capture verification modes.

16. The method of claim 1, wherein:
    selecting the one or more capture verification modes comprises selecting a first capture verification mode and a second capture verification mode; and
    implementing capture verification comprises using the second capture verification mode to confirm the first capture verification mode.

17. The method of claim 1, further comprising periodically re-evaluating the plurality of capture verification modes.

18. The method of claim 1, further comprising re-evaluating the plurality of capture verification modes responsive to an event that may alter capture verification effectiveness.

* * * * *